US008399027B2

(12) United States Patent
Burton et al.

(10) Patent No.: US 8,399,027 B2
(45) Date of Patent: *Mar. 19, 2013

(54) SILVER COATINGS AND METHODS OF MANUFACTURE

(75) Inventors: Scott A. Burton, Woodbury, MN (US); David R. Holm, Hudson, WI (US)

(73) Assignee: 3M Innovative Properties Company, Saint Paul, MN (US)

( * ) Notice: Subject to any disclaimer, the term of this patent is extended or adjusted under 35 U.S.C. 154(b) by 899 days.

This patent is subject to a terminal disclaimer.

(21) Appl. No.: 11/331,954

(22) Filed: Jan. 13, 2006

(65) Prior Publication Data

US 2006/0233889 A1     Oct. 19, 2006

Related U.S. Application Data

(63) Continuation-in-part of application No. 11/105,954, filed on Apr. 14, 2005, now abandoned.

(51) Int. Cl.
*A61K 33/38* (2006.01)
*A61K 31/74* (2006.01)
*A61K 31/28* (2006.01)

(52) U.S. Cl. .................. 424/618; 424/78.06; 514/495
(58) Field of Classification Search .................. 424/618, 424/78.06; 514/495
See application file for complete search history.

(56) References Cited

U.S. PATENT DOCUMENTS

| | | | |
|---|---|---|---|
| 2,396,514 A | 3/1946 | Kreidl et al. | |
| 2,521,713 A | 9/1950 | Goetz | |
| 2,689,809 A | 9/1954 | Fessler | |
| 2,785,106 A | 3/1957 | Mendelsohn | |
| 2,791,518 A | 5/1957 | Stokes et al. | |
| 2,813,056 A | 11/1957 | Davis et al. | |
| 2,813,059 A | 11/1957 | Davis et al. | |
| 2,934,066 A | 4/1960 | Stowasser | |
| 2,981,640 A | 4/1961 | Hill | |
| 3,092,552 A | 6/1963 | Romans | |
| 3,380,848 A | 4/1968 | Horowitz | |
| 3,385,654 A | 5/1968 | Yardney et al. | |
| 3,685,993 A | 8/1972 | Mukherjee | |
| 3,761,590 A | 9/1973 | Fox, Jr. | |
| 3,800,792 A | 4/1974 | McKnight et al. | |
| 3,911,115 A | 10/1975 | Hadhanyi | |
| 4,024,312 A | 5/1977 | Korpman | |
| 4,080,210 A | 3/1978 | Asada | |
| 4,226,232 A | 10/1980 | Spence | |
| 4,340,043 A | 7/1982 | Seymour | |
| 4,396,512 A | 8/1983 | Beauman et al. | |
| 4,446,124 A | 5/1984 | Fox, Jr. et al. | |
| 4,592,920 A | 6/1986 | Murtfeldt | |
| 4,599,226 A | 7/1986 | Fox, Jr. et al. | |
| 4,603,152 A | 7/1986 | Laurin et al. | |
| 4,646,730 A | 3/1987 | Schonfeld et al. | |
| 4,652,465 A | 3/1987 | Koto et al. | |
| 4,728,323 A | 3/1988 | Matson | |
| 4,864,042 A | 9/1989 | Armstrong | |
| 4,902,503 A | 2/1990 | Umemura et al. | |
| 4,902,565 A | 2/1990 | Brook | |
| 4,906,466 A | 3/1990 | Edwards et al. | |
| 5,088,978 A | 2/1992 | Hillman | |
| 5,147,339 A | 9/1992 | Sundström | |
| 5,232,748 A | 8/1993 | Horowitz et al. | |
| 5,254,285 A | 10/1993 | Fujita | |
| 5,326,567 A | 7/1994 | Capelli | |
| 5,393,831 A * | 2/1995 | Hudson ......................... 525/55 |
| 5,413,788 A | 5/1995 | Edwards et al. | |
| 5,429,819 A | 7/1995 | Oka et al. | |
| 5,454,886 A | 10/1995 | Burrell et al. | |
| 5,470,585 A | 11/1995 | Gilchrist | |
| 5,512,041 A | 4/1996 | Bogart | |
| 5,516,581 A | 5/1996 | Kreckel et al. | |
| 5,599,648 A | 2/1997 | Kondo | |
| 5,681,575 A | 10/1997 | Burrell et al. | |
| 5,695,857 A | 12/1997 | Burrell et al. | |
| 5,709,870 A | 1/1998 | Yoshimura et al. | |
| 5,744,151 A * | 4/1998 | Capelli ......................... 424/405 |
| 5,770,255 A | 6/1998 | Burrell et al. | |
| 5,803,086 A | 9/1998 | Scholz et al. | |
| 5,830,496 A * | 11/1998 | Freeman ...................... 424/445 |
| 5,848,995 A | 12/1998 | Walder | |
| 5,876,489 A | 3/1999 | Kunisaki et al. | |
| 5,897,673 A | 4/1999 | Nishida | |
| 5,897,694 A | 4/1999 | Woolf | |
| 5,958,440 A | 9/1999 | Burrell et al. | |
| 5,985,308 A | 11/1999 | Burrell et al. | |
| 6,017,553 A | 1/2000 | Burrell et al. | |
| 6,039,940 A | 3/2000 | Perrault et al. | |
| 6,087,549 A | 7/2000 | Flick | |
| 6,126,931 A | 10/2000 | Sawan et al. | |
| 6,156,678 A | 12/2000 | Mukaida et al. | |
| 6,183,770 B1 | 2/2001 | Muchin | |
| 6,194,332 B1 | 2/2001 | Rock et al. | |
| 6,201,164 B1 | 3/2001 | Wulff et al. | |
| 6,224,983 B1 * | 5/2001 | Sodervall et al. ............ 428/461 |
| 6,267,590 B1 | 7/2001 | Barry et al. | |
| 6,277,892 B1 | 8/2001 | Deckner et al. | |
| 6,288,076 B1 | 9/2001 | Kostyniak et al. | |
| 6,297,335 B1 | 10/2001 | Funk et al. | |
| 6,333,093 B1 | 12/2001 | Burrell et al. | |
| 6,355,858 B1 | 3/2002 | Gibbins | |
| 6,436,420 B1 | 8/2002 | Antelman | |
| 6,468,521 B1 | 10/2002 | Pedersen et al. | |
| 6,548,727 B1 | 4/2003 | Swenson | |

(Continued)

FOREIGN PATENT DOCUMENTS

CA      2428922      11/2004
CA      2460585      11/2004

(Continued)

OTHER PUBLICATIONS

Hawley's Condensed Chemical Dictionary, 2002, methylene chloride.*

(Continued)

*Primary Examiner* — Abigail Fisher
(74) *Attorney, Agent, or Firm* — Trisha D. Adamson

(57) ABSTRACT

A silver composition comprising silver sulfate and a method of coating the composition on a substrate is disclosed.

28 Claims, No Drawings

U.S. PATENT DOCUMENTS

| | | |
|---|---|---|
| 6,592,888 B1 | 7/2003 | Jensen et al. |
| 6,605,751 B1 | 8/2003 | Gibbins et al. |
| 6,669,981 B2 | 12/2003 | Parsons et al. |
| 6,706,260 B1 | 3/2004 | Tanaka |
| 6,716,895 B1 | 4/2004 | Terry |
| 6,797,743 B2 | 9/2004 | McDonald et al. |
| 6,843,784 B2 | 1/2005 | Modak et al. |
| 7,745,509 B2 | 6/2010 | Burton et al. |
| 8,124,826 B2 | 2/2012 | Addison |
| 2001/0010016 A1 | 7/2001 | Modak et al. |
| 2002/0004951 A1 | 1/2002 | Auger |
| 2002/0051823 A1 | 5/2002 | Yan et al. |
| 2002/0073891 A1 | 6/2002 | Parsons et al. |
| 2002/0123710 A1 | 9/2002 | Worthley |
| 2003/0021832 A1 | 1/2003 | Scherr |
| 2003/0026848 A1 | 2/2003 | Joshi |
| 2003/0032765 A1 | 2/2003 | McDonald et al. |
| 2003/0043341 A1* | 3/2003 | Turner et al. .............. 351/160 R |
| 2003/0049300 A1 | 3/2003 | Terry |
| 2003/0054046 A1* | 3/2003 | Burrell et al. ................. 424/618 |
| 2003/0108608 A1 | 6/2003 | Laridon et al. |
| 2003/0113378 A1 | 6/2003 | Laridon et al. |
| 2003/0118624 A1 | 6/2003 | Jackson et al. |
| 2003/0118733 A1 | 6/2003 | Jackson et al. |
| 2003/0175503 A1 | 9/2003 | Lucast et al. |
| 2003/0180346 A1* | 9/2003 | Woods ........................... 424/446 |
| 2003/0185889 A1 | 10/2003 | Yan et al. |
| 2003/0190851 A1* | 10/2003 | Yan et al. ...................... 442/123 |
| 2004/0126433 A1 | 7/2004 | Parsons et al. |
| 2004/0180093 A1 | 9/2004 | Burton |
| 2004/0214809 A1 | 10/2004 | Capelli |
| 2004/0229034 A1 | 11/2004 | Djokic |
| 2005/0123590 A1 | 6/2005 | Burton |
| 2005/0123621 A1 | 6/2005 | Burton |
| 2005/0124724 A1 | 6/2005 | Burton et al. |
| 2006/0034899 A1 | 2/2006 | Ylitalo |
| 2006/0035039 A1 | 2/2006 | Ylitalo |
| 2006/0141015 A1 | 6/2006 | Tessier et al. |
| 2006/0173087 A1 | 8/2006 | Hyde et al. |
| 2006/0233888 A1 | 10/2006 | Burton |
| 2006/0233889 A1 | 10/2006 | Burton et al. |
| 2007/0166399 A1 | 7/2007 | Burton et al. |
| 2008/0279960 A1 | 11/2008 | Burton et al. |
| 2010/0098949 A1 | 4/2010 | Burton |
| 2010/0233273 A1 | 9/2010 | Burton |

FOREIGN PATENT DOCUMENTS

| | | |
|---|---|---|
| CA | 4460585 | 11/2004 |
| CN | 1123665 | 6/1996 |
| CN | 1128188 | 8/1996 |
| CN | 1241662 | 1/2000 |
| CN | 1291667 | 4/2001 |
| CN | 1308102 | 8/2001 |
| CN | 1317033 | 10/2001 |
| CN | 1328819 | 1/2002 |
| CN | 1348032 | 5/2002 |
| CN | 1369206 | 9/2002 |
| CN | 1379146 | 11/2002 |
| CN | 1214867 | 1/2004 |
| CN | 1241662 | 8/2004 |
| CN | 1322874 C | 1/2005 |
| CN | 1605676 | 4/2005 |
| DE | 2 260 536 | 7/1974 |
| DE | 273 846 | 11/1989 |
| DE | 42 26 810 C1 | 1/1994 |
| DE | 199 58 697 | 6/2001 |
| DE | 10023336 | 9/2001 |
| EP | 0 255 248 A2 | 2/1988 |
| EP | 0 512 855 A2 | 5/1991 |
| EP | 0 272 149 | 3/1992 |
| EP | 0 984 698 B1 | 4/2003 |
| GB | 591 440 | 8/1947 |
| GB | 769799 | 3/1957 |
| GB | 2 127 389 | 4/1984 |
| GB | 2 127 389 A | 4/1984 |
| GB | 2 134 791 A | 8/1984 |
| GB | 2 272 641 A | 5/1994 |
| JP | 54-074841 | 6/1979 |
| JP | 54-152696 | 12/1979 |
| JP | 63012723 | 2/1988 |
| JP | 01-274807 | 11/1989 |
| JP | 02-004376 | 1/1990 |
| JP | 02-303818 | 12/1990 |
| JP | 03193047 | 8/1991 |
| JP | 04-007004 | 1/1992 |
| JP | 04-163137 | 6/1992 |
| JP | 4-272754 | 9/1992 |
| JP | 4-272764 | 9/1992 |
| JP | 4-272765 | 9/1992 |
| JP | 5-17617 | 1/1993 |
| JP | 5-57002 | 3/1993 |
| JP | 05-059662 | 3/1993 |
| JP | 06-313266 | 11/1994 |
| JP | 07-149943 | 6/1995 |
| JP | 08-029944 | 2/1996 |
| JP | 2501199 | 3/1996 |
| JP | H09505112 | 5/1997 |
| JP | 10-165809 | 6/1998 |
| JP | 11-507679 | 7/1999 |
| JP | 2001-040222 | 2/2001 |
| JP | 2002-523565 | 7/2002 |
| JP | 2002-233708 | 8/2002 |
| JP | 2002-524203 | 8/2002 |
| JP | 2005-002033 | 6/2005 |
| JP | 2007511313 | 5/2007 |
| WO | WO 84/01721 | 5/1984 |
| WO | WO 89/02754 | 4/1989 |
| WO | WO 92/18098 | 10/1992 |
| WO | WO 93/12275 A1 | 6/1993 |
| WO | WO 95/13704 | 5/1995 |
| WO | WO 96/01119 A1 | 1/1996 |
| WO | WO 96/39464 | 12/1996 |
| WO | WO 97/00163 | 1/1997 |
| WO | WO 97/02038 A1 | 1/1997 |
| WO | WO 98/41095 A2 | 9/1998 |
| WO | WO 98/41095 A3 | 9/1998 |
| WO | WO 99/15101 | 4/1999 |
| WO | WO 00/01424 | 1/2000 |
| WO | WO 00/09173 | 2/2000 |
| WO | WO 00/09173 A1 | 2/2000 |
| WO | WO 00/49219 | 8/2000 |
| WO | WO 00/71183 A1 | 11/2000 |
| WO | WO 01/24839 | 4/2001 |
| WO | WO 01/43549 A2 | 6/2001 |
| WO | WO 01/43549 A3 | 6/2001 |
| WO | WO 01/43788 | 6/2001 |
| WO | WO 02/18003 | 3/2002 |
| WO | WO 02/18699 A1 | 3/2002 |
| WO | WO 02/24240 A1 | 3/2002 |
| WO | WO 02/43743 | 6/2002 |
| WO | WO 02/ 43743 A1 | 6/2002 |
| WO | WO 0247737 A1 * | 6/2002 |
| WO | WO 02/062403 | 8/2002 |
| WO | WO 02/078755 | 10/2002 |
| WO | WO 02/087645 | 11/2002 |
| WO | WO 02/090025 A1 | 11/2002 |
| WO | WO 03/002089 A1 | 1/2003 |
| WO | WO 03/020231 | 3/2003 |
| WO | WO 03/022317 | 3/2003 |
| WO | WO 03/046273 A1 | 6/2003 |
| WO | WO 03/047636 | 6/2003 |
| WO | WO 03/053484 | 7/2003 |
| WO | WO 03/060008 | 7/2003 |
| WO | WO 03/080231 A1 | 10/2003 |
| WO | WO 03/080911 | 10/2003 |
| WO | WO 2004/017738 A1 | 3/2004 |
| WO | WO 2004/080499 A1 | 9/2004 |
| WO | WO 2004/101014 | 11/2004 |
| WO | WO 2004/101014 A2 | 11/2004 |
| WO | WO 2004/101014 A3 | 11/2004 |
| WO | WO 2004/112850 | 12/2004 |
| WO | WO 2005/038122 A1 | 4/2005 |
| WO | WO 2005/056067 | 6/2005 |
| WO | WO 2005/056067 A1 | 6/2005 |

| WO | WO 2005/056070 | | 6/2005 |
|---|---|---|---|
| WO | WO 2006/113052 | A2 | 10/2006 |
| WO | WO 2006/113052 | A3 | 10/2006 |

OTHER PUBLICATIONS

Antelman "Silver (II, III) Disinfectants." Soap/Cosmetics/Chemical Specialties. Mar. 1994. pp. 52-59.
Furr et al. "Antibacterial Activity of Actisorb Plus, Actisorb and Silver Nitrate." 1994 *J. Hosp. Infect.* 27:201-208.
Nomiya et al. "Syntheses, Crystal Structures and Antimicrobial Activities of Polymeric Silver(1) Complexes with Three Amino-Acids [aspartic acid ($H_2$asp), Glycine (Hgly) and Asparagine (Hasn)]." 2002 *J. Chem. Soc. Dalton Trns.* pp. 2483-2490.
Thomas et al. "A Comparison of the Antimicrobial Effects of Four Silver-Containing Dressings on Three Organisms." 2003 *J. Wound Care* 12(3):101-107.
Tredget et al. "A Matched-Pair, Randomized Study Evaluating the Efficacy and Safety of Acticoat Silver-Coated Dressing for the Treatment of Burn Wounds." 1998 *J. Burn Care and Rehab.* 19(6):531-537.
Wright et al. "Wound Management in an Era of Increasing Bacterial Antibiotic Resistance: A Role for Topical Silver Treatment." 1998 *AJIC* 26(6):572-577.
International Search Report for PCT Application No. PCT/US2006010977, filed on Mar. 24, 2006; and entitled "Silver Coatings and Methods of Manufacture."
U.S. Appl. No. 11/550,434, filed Oct. 18, 2002; and entitled "Antimicrobial Articles and Methods of Manufacture."
U.S. Appl. No. 11/550,440, filed Oct. 18, 2002; and entitled "Antimicrobial Articles and Methods of Manufacture."
European Office Action dated Jul. 21, 2008 for European Patent Application No. 06 739 656.4-1219 (5 pgs).
"Solubility of Silver Compounds in Water," Salt Lake Metals, Salt Lake City, UT. [online]. [Retrieved Oct. 23, 2009]. Retrieved from the Internet: <http://www.saltlakemetals.com/Solubility_Of_Silver_Compounds.htm>; 2 pgs.
PCT International Search Report ISA210.
Handbook of Chemistry, Norbert Adolph Lange, Ph. D., Handbook Publisher's, Inc., 2nd Edition, 1937.
Lange's Handbook of Chemistry, John A. Dean, McGraw-Hill, Inc., 14th Edition, 1992.
Welle, "Migration and Sensory Changes of Packaging Materials Caused by Ionising Radiation", Radiation Physics and Chemistry, 2002, vol. 63, pp. 841-844.
Gibbins et al.; Clinical study entitled "An In-Vitro Comparison of a New Antimicrobial Polyacrylate Absorbent Wound Dressing Containing Silver with the Silver-Containing Antimicrobial Film Dressings" from AcryMed dated Oct. 1999 (7 pgs.) printed Sep. 27, 2001.
Calvert et al.; "Photochemistry"; Chapter II; John Wiley & Sons Inc. (1966) pp. 27-125.
Sheet entitled "Rheology Modifiers" from Ciba Specialty Chemicals 2001 (1 pg.).
Brochure entitled "Ciba® SALCARE® SC95—Rheology Modifier" from Ciba Specialty Chemcials 2001 (5 pgs.).
Feng et al; "A mechanistic study of the antibacterial effect of silver ions on *Escherichia coli* and *Staphylococus aureus*"; J. Biomed Mater Res 15 (52); (pp. 662-668 (2000).
Lansdown, A.; "Silver 1: its antibacterial properties and mechanism of action"; Journal of Wound Care; vol. 11; No. 4, Apr. 2002; pp. 125-130.
Lansdown, A.; "Silver 2: toxicity in mammals and how its products aid wound repair"; Journal of Wound Care; vol. 11, No. 5, May 2002; pp. 173-177.
Nesbitt et al.; "Solubility Studies of Silver Sulfadiazine"; Journal of Pharmaceutical Sciences; vol. 66, No. 4, Apr. 1977; pp. 519-522.
Odian, G.; "Principles of Polymerization"; $3^{rd}$ Edition; 1991; 16 pgs. Table of Contents and pp. 352-353.
Russell et al.; "Antimicrobial Activity and Action of Silver"; Progress in Medicinal Chemistry; vol. 31; 1994; pp. 351-370.
Wright et al.; "The Comparative Efficacy of Two Antimicrobial Barrier Dressings": In vitro Examination of Two Controlled Release of Silver Dressings; Wounds 10(6); pp. 179-188, 1998 © Health Management Publications, Inc.
D. Acel; "Concerning the Oligodynamic Effect of Metals"; Biochemical Magazine; pp. 23-26; Aug. 21, 1920.
J. Gibbarb, "Public Health Aspects of the Treatment of Water and Beverages With Silver"; American Journal of Public Health; Feb., 1937; vol. 27, pp. 112-119.
N. Grier; "Silver and Its Compound"; Disinfection, Sterilization and Preservation ($3^{rd}$ Ed.) Ch. 18 , pp. 375-389, 1983.
J. He et al.; "Facile In Situ Synthesis of Noble Metal Nanoparticles in Porous Cellulose Fibers"; Chem. Mater. 2003, vol. 15, No. 23, pp. 4401-4406.
"The Carbohydrates *Chemistry and Biochemistry*"; Second Edition; Edited by W. Pigman and D. Horton; 1970; pp. 426-427.
M. Fetizon et al.; "Proceeding of the Weekly Sessions of the Academy of Sciences"; Organic Chemistry: Oxidation by Silver Carbonates Deposited on Celite: Degradation of D-glactose into D-lyxose; Series C, 275; Sep. 18, 1972; pp. 621-623.
ASTM D2244-05, "Standard Practice for Calculation of Color Tolerances and Color Differences from Instrumentally measured Color Coordinates," *Annual Book of ASTM Standards*, Oct. 1, 2005, pp. 239-248.
ASTM D 2369-03, "Standard Test Method for Volatile Content of Coatings," *Annual Book of ASTM Standards*, vol. 15.05, pp. 277-280, 2003.
ASTM D3759-83, "Standard Test Method for Tensile Strength and Elongation of Pressure-Sensitive Tapes," *Annual Book of ASTM Standards*, vol. 14.02, pp. 662-670.
ASTM D3985-02, "Standard Test Method for Oxygen Gas Transmission Rate Through Plastic Film and Sheeting Using a Coulometric Sensor," *Annual Book of ASTM Standards*, May 10, 2002, pp. 460-465.
ASTM F1249-01, "Standard Test Method for Water Vapor Transmission Rate Through Plastic Film and Sheeting Using a Modulated Infrared Sensor," *Annual Book of ASTM Standards*, vol. 11.03, pp. 1289-1293, 2001.
Dean, John A., "Section 3.2," *Lange's Handbook of Chemistry*, McGraw-Inc., Fifteenth Edition, 1998, pp. 3.11, 3.64 and 3.65.
Yuranova et al., Antibacterial textiles prepared by RF-plasma and vacuum-UV mediated deposition of silver, Journal of Photochemistry and photo biology A: Chemistry, vol. 161, Issue 1, Nov. 17, 2003, pp. 27-34, ISSN 1010-6030, 10.1016/S1010-6030(03)00204-1.

* cited by examiner

SILVER COATINGS AND METHODS OF MANUFACTURE

CROSS-REFERENCE TO RELATED APPLICATIONS

This application is a Continuation-In-Part of U.S. patent application Ser. No. 11/105,954, filed on Apr. 14, 2005 now abandoned, which is incorporated herein in its entirety.

BACKGROUND

While wounds heal more effectively in moist environments, bacterial infection poses increased risk. Use of antibiotics to treat bacterial infections can build bacterial resistance. Silver compounds are known to impart antimicrobial effects to a surface with minimal risk of developing bacterial resistance. Silver is delivered to the surface by sustained release of silver ions from the surface when in contact with moist environments, such as a wound bed.

Silver compositions, such as silver nitrate and silver sulfadiazine, are effective antimicrobials used in a variety of applications. However, they are typically not light stable, leave a stain on skin with which they come into contact, and in the case of silver nitrate, can be quickly depleted in an aqueous environment. Use of silver salts as antimicrobials have included the use of stabilizing agents to increase light stability such as those described in U.S. Pat. No. 2,791,518 (Stokes et al.) (using a first solution of ammonia, silver nitrate and barium nitrate; and a second solution of sodium chloride and sodium sulfate); and in U.S. Pat. No. 6,669,981 (Parsons et al.) (a silver salt in water/organic solvent followed by one or more stabilizing agents (e.g., ammonium salts, thiosulphates, chlorides and/or peroxides)).

SUMMARY

The present invention is directed to a method of coating silver sulfate on a substrate. The coated silver sulfate compositions are color stable without the addition of a stabilizing agent under readily achievable storage conditions.

In one aspect, the present invention provides a method of making an antimicrobial article. The method includes preparing a composition comprising silver sulfate with the proviso that stabilizing agents are present in the composition in an amount less than 100 ppm; coating the silver sulfate composition on a substrate; and drying the coated substrate at a temperature that causes the silver sulfate composition to develop an initial color; wherein the dried silver sulfate composition is color stable.

In another aspect, an antimicrobial medical article is provided. The article includes a silver sulfate composition coated on a substrate, wherein stabilizing agents are present in the antimicrobial article in an amount less than 1000 ppm, and wherein the coated silver sulfate composition is color stable.

In another aspect, a method of making an antimicrobial article is provided that includes: preparing a composition of silver sulfate and water; coating the silver sulfate composition on a substrate; drying the coated substrate at a temperature that causes the silver sulfate composition to develop an initial color; and maintaining the dried silver sulfate composition at a relative humidity of no more than 50%; wherein the antimicrobial article is color stable.

In another aspect, a method of making an antimicrobial article is provided that includes: preparing a composition comprising silver sulfate; coating the silver sulfate composition on a substrate; and drying the coated substrate at a temperature that causes the silver sulfate composition to develop an initial color; wherein the dried silver sulfate composition is color stable; and wherein stabilizing agents are present in the antimicrobial article in an amount less than 1000 ppm.

In another aspect, the silver compound can be coated on a substrate, such as a nonwoven gauze, a woven gauze, a film, and a hydrocolloid.

In this context, "color stable" means that the color of the dried silver sulfate composition coated on a substrate does not exhibit a significant change in color and/or color homogeneity to the human eye over time (preferably at least 4 hours, more preferably at least 8 hours, even more preferably at least 48 hours, and even more preferably at least 1 week) when compared to the same coated composition on a substrate that has not been exposed to light (e.g., fluorescent, natural, UV). Preferably, "color stable" means that the color of the dried silver sulfate composition coated on a substrate does not exhibit a perceptible change to the human eye over time (preferably at least 4 hours, more preferably at least 8 hours, even more preferably at least 48 hours, and even more preferably at least 1 week) when compared to the same coated composition on a substrate that has not been exposed to light (e.g., fluorescent, natural, UV).

Color change can be evaluated in a number of ways using a number of grading scales. For example, color change can be evaluated by visual ranking under fluorescent lighting. Samples are compared to color standards and given a rating based on that visual comparison. In this ranking scale, 0, 1, and 2 are classified as "whitish" including white to cream, 3 through 5 are classified as "yellowish" including light yellow to golden yellow, and 6 through 10 are classified as rust to dark brown. Color change is the difference in ratings obtained by subtracting the initial rating from the rating after treatment. Positive ratings represent a darkening in appearance and negative ratings represent a lightening in appearance. A color change on this scale of 1 or less is acceptable as long as the color is substantially homogeneous. If the color is non-homogeneous, even a color change of 0.5 is considered a "significant" and unacceptable change.

Color change can also be measured using a colorimeter such as a Minolta Chroma Meter (CR-300, manufactured by Konica Minolta Photo Imaging U.S.A., Inc., Mahwah, N.J.) using tristimulus values. A a color change on this scale in the "Y" value of 15% or less is acceptable as long as the color is homogeneous. If the color is non-homogeneous, even a color change of 5% in the "Y" value is considered a "significant" and unacceptable change.

Color change can also be measured using a colorimeter according to ASTM D2244. The resulting CIELAB color difference (DE*), between the sample after exposure for the indicated period of time and the unexposed sample can be determined. For purposes of reference only, a DE*, or color change of about 2 units is just detectable by the naked eye whereas a DE* of 20 or greater represents a substantial or "significant" and unacceptable color change.

"Room temperature" means an average room temperature, typically 23 deg C.+/−2 deg C.

"Relative humidity" the ratio of the quantity of water vapor present in the atmosphere to the quantity that would saturate the atmosphere at the given temperature.

As used herein, "a," "an," "the," "at least one," and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The above summary of the present invention is not intended to describe each disclosed embodiment or every implementation of the present invention. The description that follows more particularly exemplifies illustrative embodiments.

DETAILED DESCRIPTION OF ILLUSTRATIVE EMBODIMENTS OF THE INVENTION

The present invention provides a method for coating silver sulfate, by dissolving silver sulfate in an aqueous-based composition, coating the composition on a substrate, and drying the coated substrate. The substrate coated with silver sulfate remains stable to light (e.g., visible, UV) and heat without the addition of traditional stabilizing agents such as ammonia, ammonium salts (e.g., ammonium acetate, ammonium sulfate, and ammonium carbonate), thiosulfates, water insoluble salts of metals (e.g., halides such as chlorides), peroxides, magnesium trisilicate, and/or polymers. Preferably, any component that would function as a stabilizing agent is present in amounts less than 100 ppm, more preferably less than 50 ppm, most preferably less than 20 ppm, based on the total weight of the silver sulfate composition. Alternatively, any component that would function as a stabilizing agent is present in amounts less than 1000 ppm, more preferably less than 500 ppm, most preferably less than 100 ppm, based on the total weight of the antimicrobial article comprising a dried silver sulfate composition coated on a substrate.

The resultant solution containing the silver sulfate solution can be coated on a substrate, preferably an absorbent substrate, although nonabsorbent substrates can also be used. The coated substrate is dried to drive off the volatile components, such as water and organic solvents (e.g., methanol, ethanol, isopropanol, acetone, or other organic solvents that are miscible with water). Drying can be accomplished at room temperature or by heating the coated substrate. Heat will speed the drying process. In a preferred embodiment, the coated substrate is dried at temperatures below 190° C., more preferably below 170° C., even more preferably below 140° C., to minimize reduction of the silver compounds, and also prevent the oxidation of a cellulosic material, when used as a substrate.

Further, tensile strength of an oxidizable substrate (such as cotton) is maximized when the silver sulfate composition on the substrate is dried at a low temperature, preferably less that 140° C., more preferable at less than 100° C., and most preferably at less than 70° C.

Once dried, the substrate remains coated with the silver sulfate. The coated composition typically contains silver sulfate in a major amount. Low levels of silver metal may be present in amounts of preferably less than 20 wt %, and more preferably less than 10 wt %, based on the total weight of the silver components in the composition. In some embodiments, the choice of starting materials and drying temperatures results in a coating that leaves no residue with essentially only the silver sulfate remaining on the substrate, and all other components of the silver solution removed from the substrate upon drying.

When applied, the silver sulfate solution penetrates and impregnates the interior of the substrate. For example, when gauze is used, the silver solution impregnates between the fibers of the gauze.

The concentration of silver sulfate on the substrate is a function of the amount of silver sulfate in solution, the total amount of solution applied onto a unit area of the substrate, and the drying temperature. The silver sulfate concentration on the substrate is typically less than 30 $mg/cm^2$, and in certain embodiments less than 5 $mg/cm^2$. In a preferred embodiment, the silver sulfate concentration on the substrate ranges from 0.001 $mg/cm^2$ to 5 $mg/cm^2$, and in certain embodiments from 0.001 $mg/cm^2$ to 1 $mg/cm^2$.

The substrate can be a woven or nonwoven material made of natural or synthetic compounds. The substrate can be a porous or nonporous film. It can be a knitted fabric, a foam, or a hydrocolloid, for example.

Cellulosic materials such as polysaccharide or modified polysaccharide, regenerated cellulose (such as rayon), paper, cotton, that available under the trade designation TENCEL, carboxymethyl cellulose may be used. Further, polyvinylpyrrolidone, polyvinyl alcohol, polyvinyl ether, polyacrylate, polyacrylamide, collagen, gelatin, may be used. Non-absorbent substrates may also be used including, but not limited to, nylon, polyester, polyethylene, and polypropylene.

Other suitable materials for the substrate include polyacrylonitrile, polyvinylidene difluoride, polytetrafluoroethylene, polyoxymethylene, polyvinyl chloride, polycarbonate, styrene-ethylenebutylene-styrene elastomer, styrene-butylene-styrene elastomer, styrene-isoprene-styrene elastomer, and combinations thereof. Other substrate materials are disclosed herein below. Various combinations of materials may be included within the substrate. In certain embodiments, the substrate includes a material selected from the group consisting of a cellulosic material, nylon, polyester fiber, and combinations thereof. In certain embodiments, the substrate includes a cellulosic material. In certain embodiments, the cellulosic substrate includes cotton.

The method provides a silver sulfate solution for coating on a substrate without using an acid. The presence of acid can hydrolyze the cellulosic material. This aspect of the process allows the coating to be applied without weakening the cellulosic substrate. Preferably the coating solution has a pH of at least 4, more preferably at least 5. Preferably, the coating solution has a pH of no greater than 9.

Elevated temperatures can also accelerate the oxidation of cellulose by a silver salt, resulting in such affects as lowering the tensile strength and changing the color of the silver sulfate composition on the substrate. The color change on a cellulosic material, such as cotton, is likely due to the reduction of silver salt to silver metal with an accompanying oxidation of the cellulose substrate. The oxidized cotton has lower tensile strength.

If silver sulfate is coated on a cellulosic substate or other easily oxidizable substrate (e.g., a silver nitrate oxidizable substrate), the article will change color in proportion to the drying temperature and the time in the drying device, such as an oven. Generally, no color change is observed when the substrate coated with the silver sulfate composition is dried below approximately 100° C. for 15 minutes. For example, when wetted cotton is dried at an oven temperature greater than approximately 100° C., the cotton substrate darkens in proportion to the oven temperature and turns yellow then brown then dark brown.

If a synthetic substrate such as polyester, which is not easily oxidized, is coated with silver sulfate coating solution and dried, the polyester will remain white even when dried at temperature above 100° C.

The silver compositions, once coated, are preferably color stable (i.e., stable to light as defined herein). In addition, preferably the compositions are also stable to at least one of the following: heat and/or moisture. Regardless of substrate choice, the coated silver sulfate composition is color stable. The initial color that the silver sulfate solution develops after drying at a particular temperature will remain without appreciable change over time (preferably for at least 4 hours, more preferably for at least 8 hours, even more preferably at least 48 hours, and even more preferably at least 1 week), either with or without exposure to light.

The color stability of the coated silver sulfate composition provides a couple advantages. The color stability provides an indication to the end user that the product is of consistent high quality. Further, the color stability indicates that the form of silver on the substrate has not appreciably changed which indicates that its performance (i.e., silver release, antimicrobial activity) is essentially constant over time (preferably for at least 4 hours, more preferably for at least 8 hours, even more preferably at least 48 hours, and even more preferably at least 1 week).

Such compositions are useful in medical articles, particularly wound dressings and wound packing materials, although a wide variety of other products can be coated with the silver sulfate compositions.

Stability of the silver sulfate coated substrate is prolonged and/or increased when the relative humidity at room temperature is maintained at 50% or lower; more preferably at 30% or lower; and most preferably at 20% or lower. Relative humidity can be reduced to 30%, and preferably to 20%, or lower for the silver sulfate coated substrate by a number of methods including: 1) placing the coated substrate in an environment that has a relative humidity of 30% or lower, preferably 20% or lower, and then packaging the product in the same environment; 2) drying the mesh in an oven, then immediately packaging the mesh; and 3) addition of a desiccant within the package. Preferably, to maintain a low relative humidity in the dried silver sulfate composition, the article should be packaged in a package with a low moisture vapor transmission rate (MVTR) such as a Techni-Pouch package (Technipaq, Inc., Crystal Lake, Ill.) with a PET/Aluminum Foil/LLDPE material construction. Low relative humidity increases the thermal stability of silver sulfate treated cotton.

Silver compounds, including silver sulfate, provide sustained release of silver ions over time based in part on their limited solubility and inherent dissociation equilibrium constants. The silver sulfate composition may have other silver salts, including those that are not color stable, in varying amounts, as long as the composition when coated on the substrate remains color stable. In addition to silver sulfate, other silver compounds that may be coated on a substrate in addition to the silver sulfate include silver oxide, silver acetate, silver nitrate, silver citrate, silver chloride, silver lactate, silver phosphate, silver stearate, silver thiocyanate, silver saccharinate, silver anthranilate, and silver carbonate. Preferably, the amount of silver compounds other than silver sulfate is less than 20 wt %, more preferably less than 10 wt %, based on the total weight percentage (wt %) of the silver components in the silver sulfate composition coated on the substrate. Silver metal may also be present on the substrate.

The silver sulfate coated substrate remains stable when it contains silver sulfate in combination with other silver salts with limited color stability. Preferably, the amount of silver sulfate is at least 60 wt %, more preferably at least 75 wt %, and most preferably at least 90 wt %, based on the total weight percentage (wt %) of the silver components in the silver sulfate composition coated on the substrate.

Articles can be prepared using the silver solution described herein according to a variety of coating methods. When a porous substrate is coated, the process used typically allows the yarns, filaments, or film such as perforated or microporous film, to be coated, while leaving most of the apertures unobstructed by the composition. Depending on the structure of the support used, the amount of solution employed will vary over a wide range.

The silver sulfate coating solution is prepared by mixing silver sulfate and distilled water. The silver sulfate coating solution can have a range of concentrations up to a water solubility of about 0.6% at room temperature. Optionally, higher concentrations of silver sulfate can be obtained by dissolving silver sulfate in hot water. Optionally sulfate in other forms may be added, such as sodium sulfate.

The process can be accomplished as a continuous process, or it can be done in a single step or with a single coating solution. The process to apply the coating does not require elevated temperatures, and can be applied at temperatures less than 70° C. The coating solution can be maintained below a pH of 9, and preferably less than 7, to minimize adverse effects to the substrate. The coating solution can be maintained at a pH above 4.

According to a variant of this process, a substrate can be passed through a bath of the silver composition. The substrate covered with the silver sulfate composition is then dried, for example in an oven at a temperature sufficient to evaporate constituents of the solution. The temperature is preferably less than 190° C., more preferably less than 170° C., and most preferably less than 140° C.

The silver sulfate solution can also be coated onto a carrier web or a backing (described below) using a known coating technique such as gravure coating, curtain coating, die coating, knife coating, roll coating, or spray coating. A preferred coating method is gravure coating.

Medical Articles

The silver compositions of the present invention can be used in a wide variety of products, although they are preferably used in medical articles. Such medical articles can be in the form of a wound dressing, wound packing material, or other material that is applied directly to or contacts a wound. Other potential products include clothing, bedding, masks, dust cloths, shoe inserts, diapers, and hospital materials such as blankets, surgical drapes and gowns.

The silver compositions can be coated on various backings (i.e., a support substrate). The backing or support substrate can be porous or nonporous. The composition of the present invention can be coated on the support substrate or impregnated into it, for example.

Suitable materials are preferably flexible, and may be fabric, non-woven or woven polymeric webs, polymer films, hydrocolloids, foam, metallic foils, paper, and/or combinations thereof. More specifically, cotton gauze is useful with the silver compositions of the present invention. For certain embodiments it is desirable to use a permeable (e.g., with respect to moisture vapor), open apertured substrate (i.e., a scrim). For certain embodiments, the substrate may be a hydrocolloid, such as a hydrophilic polymer, or hydrophobic polymer matrix containing hydrophilic particles, as described in U.S. Pat. App. Pub. Nos. 2004/0180093 and 2005/0124724.

The substrates (i.e., backings) are preferably porous to allow the passage of wound fluids, moisture vapor, and air. In certain embodiments, the substrates are substantially impervious to liquid, especially wound exudate. In certain embodiments, the substrates are capable of absorbing liquid, especially wound exudate. In certain embodiments, the substrate is an apertured liquid permeable substrate.

Suitable porous substrates include knits, wovens (e.g., cheese cloth and gauze), nonwovens (including spun-bonded nonwovens, and BMF (blown micro fibers), extruded porous sheets, and perforated sheets. The apertures (i.e., openings) in the porous substrates are of sufficient size and sufficient number to facilitate high breathability. For certain embodiments, the porous substrates have at least 1 aperture per square centimeter. For certain embodiments, the porous substrates have no greater than 225 apertures per square centimeter. For certain embodiments, the apertures have an average opening size (i.e., the largest dimension of the opening) of at least 0.1 millimeter (mm). For certain embodiments, the apertures have an average opening size (i.e., the largest dimension of the opening) of no greater than 0.5 centimeter (cm).

For certain embodiments, the porous substrates have a basis weight of at least 5 grams/meter$^2$. For certain embodiments, the porous substrates have a basis weight of no greater than 1000 grams/meter$^2$, and in some embodiments no greater than 200 grams/meter$^2$.

The porous substrates (i.e., backings) are preferably flexible yet resistant to tearing. For certain embodiments, the thickness of the porous substrates is at least 0.0125 mm. For certain embodiments, the thickness of the porous substrates is no greater than 15 mm, and for certain embodiments no greater than 3 mm.

Materials of the backing or support substrate include a wide variety of materials including paper, natural or synthetic fibers, threads and yarns made from materials such as cotton, rayon, wool, hemp, jute, nylon, polyesters, polyacetates, polyacrylics, alginates, ethylene-propylene-diene rubbers, natural rubber, polyesters, polyisobutylenes, polyolefins (e.g., polypropylene polyethylene, ethylene propylene copolymers, and ethylene butylene copolymers), polyurethanes (including polyurethane foams), vinyls including polyvinylchloride and ethylene-vinyl acetate, polyamides, polystyrenes, fiberglass, ceramic fibers, and/or combinations thereof.

The backing can also be provided with stretch-release properties. Stretch-release refers to the property of an adhesive article characterized in that, when the article is pulled from a surface, the article detaches from the surface without leaving significant visible residue. For example, a film backing can be formed from a highly extensible and highly elastic composition that includes elastomeric and thermoplastic A-B-A block copolymers, having a low rubber modulus, a lengthwise elongation to break of at least 200%, and a 50% rubber modulus of not above 2,000 pounds/square inch (13.8 megapascals (MPa)). Such backings are described in U.S. Pat. No. 4,024,312 (Korpman). Alternatively, the backing can be highly extensible and substantially non-recoverable such as those described in U.S. Pat. No. 5,516,581 (Kreckel et al,).

In certain embodiments, the coated substrates of the present invention are nonadherent, although it should be understood that an adhesive (e.g., a pressure sensitive adhesive) could be added to an article coated with the solution. As used herein, the silver compositions of the present invention when coated on a substrate do not adhere significantly to wound tissue such that they do not cause pain and/or destruction of the wound tissue upon removal and display a 180° peel strength of less than 1 N/cm from steel, as described in U.S. Pat. App. Pub. No. 2005/0123590.

In certain embodiments, substrates coated with the silver composition can be covered on one or both sides by a permeable nonadherent outside layer to reduce adhesion and attachment to the wound. The nonadherent layer can be attached to the substrate, such as by coating or laminating. Alternatively, the coated substrate can be enclosed within a nonadherent layer, such as sleeve. The nonadherent layer can be made from nonadherent woven or nonwoven fabrics such as nylon or perflourinated-material coatings on cotton gauze. The nonadherent layer prevents attachment of materials from the enclosed silver coated substrate. At the same time, the nonadherent layer does not adversely affect the sustained release of silver from the coated substrate.

In another embodiment, the backing or support substrate can be composed of nonadherent material. For example, a nonadherent hydrophilic polymer can be used as the backing or support material, or coated on a permeable porous substrate, as described in U.S. Pat. Pub. Nos. 2004/0180093, 2005/0123590, and 2005/0124724.

If desired, the coated substrate can be covered with two protective films (for example, thin polyester films). These films optionally may include a nonstick treatment and can function to facilitate extraction from a package and in handling the article. If desired, the coated substrate can be cut into individual compresses, of sizes suitable for the use, packaged in sealed sachets, and sterilized.

Pressure sensitive adhesives used in medical articles can be used in articles of the present invention. That is, a pressure sensitive adhesive material could be applied to the article of this invention, for example, around the periphery, to adhere the article to the skin.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

| GLOSSARY OF COMPONENTS | | |
|---|---|---|
| Material/<br>Trade Name | Description | Source/Address |
| $Ag_2SO_4$ | Silver Sulfate FW311.80 | Aldrich, Milwaukee, WI |
| AgAc | Silver Acetate FW166.91 | Matheson, Coleman and Bell, Norwood, Ohio |
| AgLac | Silver Lactate FW196.94 | Aldrich, Milwaukee, WI |
| COTTOASE | 100% cotton, spunlaced, non-woven (<20 ppm chloride), 50 gsm | Unitika, Japan |
| SONTARA 810 | Non-woven spunlaced PET, 45 gsm | Dupont, Wilmington, DE |
| Spuntech | Non-woven spunlaced 100% cotton (700 ppm chloride ion), 50 gsm | Spuntech, Israel |
| $Na_2SO_4$ | Sodium Sulfate | Aldrich, Milwaukee, WI |
| $AgNO_3$ | Silver Nitrate | Aldrich, Milwaukee, WI |
| COLORPHAST | pH paper | EMD Chemicals, Gibbstown, N.J. |
| TENCEL | Non-woven of 100% TENCEL fibers, SX-152, white, 65 gsm, 24 mesh, (less than 40 ppm chloride) | Green Bay Nonwovens, Inc. in Green Bay, WI |

-continued

GLOSSARY OF COMPONENTS

| Material/<br>Trade Name | Description | Source/Address |
|---|---|---|
| TENCEL/PET | Non-woven 70/30 TENCEL/Polyester, 24 mesh apertured spunlaced (Grade SX-524, 38 gsm, white) | Green Bay Nonwovens in Green Bay, WI |

Example 1

A silver sulfate coating solution was prepared by placing 0.867 grams (g or gm) silver sulfate and 200 g distilled water in a glass bottle and capping the bottle and mixing at room temperature on a roller overnight. The pH of this solution was determined to be 5.1 using pH paper. The resulting silver sulfate (3000 micrograms (μg) Ag/g) solution was coated on 100% cotton spunlaced nonwoven mesh (COTTOASE, containing less than 20 ppm chloride) by transferring the solution by pipet to saturate the mesh that was contained in a polystyrene dish. The nonwoven mesh was treated with 5.5 g of the solution on a 4 inch by 5 inch (10.19 cm×12.7 cm) piece of mesh that weighed 0.65 g. Approximately one gram of coating solution dripped off of the mesh before the mesh was suspended in the oven for drying. Some additional solution dripped off the mesh in the oven (estimated at 1 g). The coated mesh was dried in a forced air oven (Memmert Universal Oven, available from Wisconsin Oven Company, East Troy, Wis.) by heating at 66° C. for 15 minutes. The resulting Example 1 was a white appearing material. Color and color changes on exposure are noted in Table 1.

Comparative Example A and B

A silver acetate (3000 μg Ag/g) solution was prepared and coated and dried on 100% cotton spunlaced nonwoven mesh (COTTOASE) following the procedure in Example 1 to give Comparative Example A. This silver acetate solution had a pH of 5.2 determined using pH paper. Color and color changes on exposure are noted in Table 1. A silver lactate (3000 μg Ag/g) solution was prepared and coated and dried on 100% cotton spunlaced non-woven mesh (COTTOASE) following the procedure in Example 1 to give Comparative Example B. This silver lactate solution had a pH of 5.3 determined using pH paper. Color and color changes on exposure are noted in Table 1. Samples of Examples 1 and Comparative Examples A and B were placed in a 20% constant humidity room and also in a 50% constant humidity room both at 23° C. and exposed to room fluorescent light. The color was noted visually before and after exposures and the results are presented in Table 1.

TABLE 1

Stability of Silver salts coated on Cotton

| Example | Silver Salt | Initial Color | Color after one week at 20% RH under fluorescent light. | Color after one week at 50% RH under fluorescent light |
|---|---|---|---|---|
| 1 | Silver sulfate | White | White | White |
| Comparative A | Silver acetate | White | Off white | Brown |
| Comparative B | Silver lactate | White | Brown | Brown |

Example 2

Non-woven spunlaced PET (Dupont SONTARA 8010; 45 grams per square meter (gsm)) was treated by coating with isopropanol. The isopropanol was removed by washing with distilled water and the resulting PET non-woven was coated with a silver sulfate solution. The silver sulfate solution was prepared as in Example 1 only sufficient $Ag_2SO_4$ was dissolved to make a 0.6 wt % $Ag_2SO_4$ solution and the sample was dried at 180° C. for 20 minutes. The resulting silver sulfate treated PET was white and did not change color after two weeks under room fluorescent lighting at room temperature and either 20% RH or 50% RH.

Example 3

Non-woven spunlaced 100% cotton (manufactured by Spuntech, containing 700 ppm chloride ion) was coated with silver sulfate (0.6 wt % $Ag_2SO_4$) solution prepared as in Example 2 and dried at 60° C. for 15 minutes. Initially the material was white. It darkened in a 4 days when at 50% RH under room fluorescent lights.

Example 4

Example 4 was prepared as in example 1 only it was dried at 140° C. for approximately 15 minutes.

Example 5

Example 5 was prepared as in Example 1 only using a silver sulfate/sodium sulfate coating solution (3000 μg Ag/g). The coating solution was prepared as described in Example 1 with 0.34 g $Na_2SO_4$ added to the coating solution. This solution had a pH of 5.3 as determined using pH paper. The cotton non-woven (COTTOASE) was coated and dried at 140° C. for approximately 15 minutes.

Dried samples of Example 4 and Example 5 were placed in a bottle with a wet paper towel (100% RH), and other samples equilibrated at a given humidity (20% RH or 50% RH) and then packaged in a low MVTR heat sealable foil package to evaluate the effect of water on color stability. Color was evaluated by visual comparison with the initial sample color after one weeks aging.

TABLE 2

Color of treated Cotton on Aging

| | | Color After One Weeks Aging at Conditions | |
|---|---|---|---|
| Conditions | Initial Color Example 4 & Example 5 | Example 4 $Ag_2SO_4$ treated cotton | Example 5 $Ag_2SO_4/Na_2SO_4$ treated cotton |
| 22° C.; 20% RH | pale yellow | pale yellow | pale yellow |
| 22° C.; 100% RH; | pale yellow | mottled yellow | mottled yellow |
| 49° C.; 20% RH | pale yellow | pale yellow | pale yellow |
| 49° C.; 50% RH | pale yellow | pale yellow | pale yellow |
| 49° C.; 100% RH | pale yellow | mottled brown | mottled brown |
| 49° C.; 100% RH | pale yellow | Brown | Brown |

Example 6

Example 6 was made by using the procedure outlined in Example 1 only the coating solution contained a mixture of silver nitrate and silver sulfate. The coating solution was made by mixing 90 g of silver sulfate aqueous solution (3000 μg Ag/g) and 10 g of silver nitrate aqueous solution (3000 μg Ag/g). This solution had a pH of 5.3 determined using pH paper. The cotton non-woven (COTTOASE) was coated with this silver sulfate/silver nitrate coating solution and then dried at 60° C. for 15 minutes. The dried mesh was white and was color stable (under room fluorescent lighting and room temperature) at 20% RH and 50% RH for more than 24 hours.

Examples 7-10

Examples 7-10 were made as in Example 1. A silver sulfate coating solution was made by mixing 0.867 g silver sulfate and 200 g distilled water. Cotton non-woven (COTTOASE) was coated with this solution and dried at the temperatures in Table 3 to make Examples 7-10.

Examples 11-14

Examples 11-14 were made as in Example 1 only a silver sulfate/sodium sulfate coating solution (3000 µg Ag/g) was used. The solution was made by mixing 0.867 g silver sulfate, 0.34 g $Na_2SO_4$, and 200 g distilled water. Cotton non-woven (COTTOASE) was coated with this solution and dried at the temperatures in Table 3 to make Examples 11-14.

Effect of drying temperature on cotton non-woven (COTTOASE) tensile strength (cross direction) and color were determined where the cotton was treated with water (Control), silver sulfate solution (3000 µg Ag/g, Examples 7-10), or silver sulfate/sodium sulfate solution (3000 µg Ag/g, Example 11-14) and dried in an oven for 15 minutes at the indicated temperatures in Table 3. Tensile Strength was determined according to ASTM Test Method No. D3759-83 and was performed using a Thwing Albert tester (Model EJA/2000, Thwing Albert Company, Philadelphia, Pa.), a sample width of 2.54 cm, a gauge length of 10.16 cm, and a crosshead speed of 12.7 cm/min. Reported is the maximum force applied to the test sample to obtain the tensile value at point of break divided by sample width. The units are force (N) per unit of sample width (cm). Tensile strength at break was run on 9 cross direction samples for each Example determination. The results in the table are the mean with standard deviations reported in parentheses.

Example 15

Example 15 was prepared as in Example 1 using cotton non-woven (COTTOASE) coated with silver sulfate (0.6 wt % $Ag_2SO_4$) solution and dried at 125° C. for approximately 25 minutes. The resulting color was light yellow. The silver treated cotton was exposed to fluorescent light for two weeks at approximately 20% RH with no color change. Silver ion release was measured using a silver ion selective electrode (Orion, available VWR International, Batavia, Ill.). Silver release of 30 mg silver ion per gram Example 15 was measured within two minutes of placing the sample in distilled water.

Example 16

A silver sulfate coating solution was prepared by placing 0.1445 g silver sulfate and 200 g distilled water in a glass bottle and capping the bottle and mixing at room temperature in a shaker overnight. The resulting silver sulfate (approximately 500 µg Ag/g) solution was coated on 100% cotton spunlaced nonwoven mesh (COTTOASE, containing less than 20 ppm chloride) by transferring the solution by pipet to saturate the mesh that was contained in a polystyrene dish. Each piece of nonwoven mesh (50 gsm) was treated with approximately 5 g of the solution on a 4-inch by 4-inch (10 cm×10 cm) piece of mesh. Approximately one gram of coating solution dripped off of the mesh before the mesh was suspended in the oven for drying. Some additional solution dripped off the mesh in the oven (estimated at 1 g). The coated mesh was dried in a forced air oven (Memmert Universal Oven, available from Wisconsin Oven Company, East Troy, Wis.) by heating at 66° C. for 12 minutes. The resulting material after drying was white in appearance. These coated samples were either wrapped in aluminum foil (protected from light), exposed to fluorescent light (Philips, F32T8/TL735, Universal/Hi-Vision, E4) in an environment of approximately 20% relative humidity environment, or exposed to fluorescent light (Philips, F32T8/TL735, Universal/Hi-Vision, K4) in an environment of 50% relative humidity. Color CIE tristimulus values of these samples were measured over time using a Minolta Chroma Meter (CR-300, manufactured by Konica Minolta Photo Imaging U.S.A., Inc., Mahwah, N.J.). The results are shown in Table 4.

TABLE 3

Effect of Drying Temperature on Tensile

| Oven Temp (° C.) | Water Control Tensile (N/cm) | Color | Silver sulfate Ex. No. | Tensile (N/cm) | color | Silver sulfate + sodium sulfate Ex. No. | Tensile (N/cm) | color |
|---|---|---|---|---|---|---|---|---|
| 60 | 3.77 (0.77) | White | 7 | 4.13 (0.63) | white | 11 | 4.17 (0.46) | white |
| 140 | 3.70 (0.53) | White | 8 | 3.42 (0.44) | tan | 12 | 3.92 (0.70) | tan |
| 160 | nr | Nr | 9 | 2.14 (0.19) | yellow | 13 | 2.59 (0.49) | yellow |
| 190 | 3.49 (0.61) | White | 10 | 0.28 (0.04) | brown | 14 | 0.63 (0.09) | brown |

Tensile-Mean (SD);
n = 9; the untreated control tensile was 3.87 (0.44) N/cm.
nr—sample not run High drying temperature affects the tensile strength and color of the silver mesh. The addition of sodium sulfate lessened the tensile strength degradation.

TABLE 4

Example 16 Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 91.49 | 93.5 | 106.7 |
| 1 | 20 | in foil | 91.92 | 93.95 | 106.9 |
| 2 | 20 | in foil | 91.83 | 93.85 | 106.8 |
| 4 | 20 | in foil | 91.98 | 94.00 | 107.2 |
| 7 | 20 | in foil | 92.43 | 94.44 | 107.7 |
| 24 | 20 | in foil | 92.31 | 94.32 | 107.4 |
| 48 | 20 | in foil | 92.65 | 94.70 | 107.9 |
| 0 | 20 | exposed | 91.56 | 93.58 | 106.4 |
| 1 | 20 | exposed | 91.86 | 93.87 | 106.7 |
| 2 | 20 | exposed | 92.03 | 94.02 | 106.7 |
| 4 | 20 | exposed | 91.00 | 92.89 | 105 |
| 7 | 20 | exposed | 90.06 | 91.81 | 102.7 |
| 24 | 20 | exposed | 86.11 | 87.52 | 95.05 |
| 48 | 20 | exposed | 83.59 | 85 | 91.01 |
| 0 | 50 | exposed | 92.06 | 94.1 | 106.9 |
| 1 | 50 | exposed | 92.08 | 94.11 | 106.7 |
| 2 | 50 | exposed | 91.86 | 93.86 | 106.1 |
| 4 | 50 | exposed | 90.79 | 92.75 | 103.5 |
| 7 | 50 | exposed | 89.8 | 91.56 | 101.3 |
| 24 | 50 | exposed | 82.7 | 83.87 | 88.89 |
| 48 | 50 | exposed | 76.83 | 77.94 | 79.08 |

Comparative Example C

Uncoated Substrate

The color CIE tristimulus values over time of the uncoated cotton substrate used in Example 16 were also measured. Exposure conditions are as indicated in Example 16. The results are included in Table 5.

TABLE 5

Comparative C, Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | exposed | 93.1 | 95.11 | 108.6 |
| 2 | 20 | exposed | 93.25 | 95.26 | 108.8 |
| 48 | 20 | exposed | 93.36 | 95.37 | 108.9 |

Comparative Example D

The color CIE tristimulus values over time at of a commercially available wound dressing were also measured during exposure to light Exposure conditions are as indicated in Example 16. This commercially available wound dressing (Aquacel Ag, LOT 5F05519; ConvaTec) contains silver chloride/silver alginate with high levels of chloride which acts as a stabilizer and has an initial off-white color. During exposure to light, the color of the sample became noticeably gray. The results from these experiments are shown in Table 6.

TABLE 6

Comparative D, Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 55.45 | 55.76 | 66.60 |
| 1 | 20 | in foil | 55.76 | 56.06 | 66.77 |
| 2 | 20 | in foil | 57.37 | 57.75 | 68.65 |
| 4 | 20 | in foil | 55.98 | 56.26 | 66.99 |
| 7 | 20 | in foil | 55.83 | 56.16 | 66.93 |
| 24 | 20 | in foil | 56.36 | 56.65 | 67.56 |
| 48 | 20 | in foil | 56.06 | 56.38 | 67.21 |
| 120 | 20 | in foil | 56.79 | 56.7 | 67.64 |
| 0 | 20 | exposed | 58.16 | 58.65 | 69.73 |
| 1 | 20 | exposed | 54.75 | 55.51 | 66.85 |
| 2 | 20 | exposed | 52.95 | 53.54 | 63.91 |
| 4 | 20 | exposed | 51.50 | 51.93 | 61.55 |
| 7 | 20 | exposed | 50.53 | 50.91 | 59.67 |
| 24 | 20 | exposed | 47.69 | 48.03 | 55.22 |
| 48 | 20 | exposed | 46.76 | 47.08 | 53.53 |
| 120 | 20 | exposed | 46.74 | 47.03 | 52.83 |
| 0 | 50 | exposed | 51.84 | 52.17 | 62.95 |
| 1 | 50 | exposed | 47.54 | 48.16 | 59.32 |
| 2 | 50 | exposed | 45.78 | 46.32 | 56.44 |
| 4 | 50 | exposed | 45.80 | 46.24 | 55.93 |
| 7 | 50 | exposed | 43.78 | 44.15 | 52.94 |
| 24 | 50 | exposed | 41.43 | 41.71 | 48.86 |
| 48 | 50 | exposed | 41.40 | 41.60 | 47.95 |
| 120 | 50 | exposed | 39.5 | 39.55 | 44.87 |

The resulting samples from Comparative Example D that were measured for silver release using the silver ion selective electrode (Orion, available VWR International, Batavia, Ill.). Samples from Comparative Example D that were exposed and some that were not exposed were measured and both had release rates of less than 0.07 mg silver ion per gram of sample for 30 minutes.

Example 17

Samples were prepared in same way as Example 16, except the silver sulfate solution was prepared by placing 0.289 g silver sulfate and 200 g distilled water in a glass bottle. This resulting silver sulfate solution was approximately 1000 µg Ag/g. The color of the samples was white. The results from color measurements using this coating solution on the same substrate as described in Example 16 are shown in Table 7. Exposure conditions are as indicated in Example 16.

TABLE 7

Example 17, Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 91.89 | 93.92 | 106.5 |
| 1 | 20 | in foil | 92.18 | 94.22 | 107 |
| 2 | 20 | in foil | 92.41 | 94.46 | 106.8 |
| 4 | 20 | in foil | 92.56 | 94.6 | 107.5 |
| 7 | 20 | in foil | 92.6 | 94.69 | 107.8 |
| 24 | 20 | in foil | 92.96 | 95 | 108.1 |
| 48 | 20 | in foil | 92.61 | 94.65 | 107.7 |
| 120 | 20 | in foil | 92.69 | 94.71 | 107.8 |
| 0 | 20 | exposed | 91.58 | 93.61 | 105.9 |
| 1 | 20 | exposed | 91.56 | 93.59 | 105.7 |
| 2 | 20 | exposed | 91.62 | 93.62 | 105.6 |
| 4 | 20 | exposed | 91.18 | 93.14 | 104.8 |
| 7 | 20 | exposed | 90.43 | 92.27 | 103.1 |
| 24 | 20 | exposed | 86.22 | 87.58 | 94.13 |

TABLE 7-continued

Example 17, Color with Time

| Exposure Time (hr) | Relative Humidity (% RH) | Exposure conditions | CIE Tristimulus Values | | |
|---|---|---|---|---|---|
| | | | X | Y | Z |
| 48 | 20 | exposed | 84.74 | 86.14 | 91.61 |
| 120 | 20 | exposed | 81.88 | 83.28 | 85.91 |
| 0 | 50 | exposed | 91.95 | 93.99 | 106.4 |
| 1 | 50 | exposed | 91.97 | 93.97 | 106.5 |
| 2 | 50 | exposed | 91.43 | 93.38 | 105.5 |
| 4 | 50 | exposed | 90.81 | 92.66 | 104 |
| 7 | 50 | exposed | 89.27 | 90.93 | 100.9 |
| 24 | 50 | exposed | 81.42 | 82.71 | 88.19 |
| 48 | 50 | exposed | 77.53 | 78.81 | 81.19 |
| 120 | 50 | exposed | 71.7 | 72.71 | 69.86 |

The samples from Example 17 that were stored at 20% relative humidity were measured for silver release into a solution of distilled water and sodium nitrate using a silver ion selective electrode (Orion, available VWR International, Batavia, Ill.). Sodium nitrate is used as an ionic strength adjustor. A sample (0.1102 g) from Example 17 that was exposed to light for 120 hours (hrs) at approximately 20% relative humidity released 4.5 mg silver ion per gram of sample within 30 minutes of placing the sample in 98 grams distilled water and 2.96 grams of 5M sodium nitrate. A sample (0.1328 g) from Example 17 that was not exposed to light (in foil for 120 hrs) released 5.5 mg silver ion per gram of sample within 30 minutes of placing the sample in 98 grams distilled water and 2.96 grams of 5M sodium nitrate.

Example 18

Samples were prepared in same way as Example 16, except the silver sulfate solution was prepared by placing 0.578 g silver sulfate and 200 g distilled water in a glass bottle. This resulting silver sulfate solution was approximately 2000 µg Ag/g. The results from color monitoring experiments using this coating solution on the same substrate as described in Example 16 are shown in Table 8. Exposure conditions are as indicated in Example 16. The initial color of the samples was white in appearance.

TABLE 8

Example 18, Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 92.11 | 94.13 | 106.8 |
| 1 | 20 | in foil | 92.23 | 94.27 | 106.8 |
| 2 | 20 | in foil | 92.26 | 94.31 | 107 |
| 4 | 20 | in foil | 92.02 | 94.1 | 106.6 |
| 7 | 20 | in foil | 92.27 | 94.32 | 107 |
| 24 | 20 | in foil | 92.31 | 94.31 | 107 |
| 48 | 20 | in foil | 92.01 | 94.06 | 106.5 |
| 0 | 20 | exposed | 92.29 | 94.32 | 107.2 |
| 1 | 20 | exposed | 92.13 | 94.11 | 106.8 |
| 2 | 20 | exposed | 91.83 | 93.78 | 106.2 |
| 4 | 20 | exposed | 91.15 | 93.05 | 104.7 |
| 7 | 20 | exposed | 90.03 | 91.73 | 102.2 |
| 24 | 20 | exposed | 86.13 | 87.5 | 95.07 |
| 48 | 20 | exposed | 83.2 | 84.58 | 90.53 |
| 0 | 50 | exposed | 92.14 | 94.18 | 107.3 |
| 1 | 50 | exposed | 91.89 | 93.4 | 106.7 |
| 2 | 50 | exposed | 91.81 | 93.79 | 106.1 |
| 4 | 50 | exposed | 90.8 | 92.69 | 104 |

TABLE 8-continued

Example 18, Color with Time

| Exposure Time (hr) | Relative Humidity (% RH) | Exposure conditions | CIE Tristimulus Values | | |
|---|---|---|---|---|---|
| | | | X | Y | Z |
| 7 | 50 | exposed | 88.92 | 90.47 | 100.6 |
| 24 | 50 | exposed | 79.99 | 81.17 | 85.49 |
| 48 | 50 | exposed | 72.72 | 73.79 | 74.38 |

Example 19

Samples were prepared in same way as Example 16, except the silver sulfate solution was prepared by placing 0.867 g silver sulfate and 200 g distilled water in a glass bottle. This resulting silver sulfate solution was approximately 3000 µg Ag/g. The color of the samples was white in appearance. The results from color monitoring experiments using this coating solution are shown in Table 9. Exposure conditions are as indicated in Example 16.

TABLE 9

Example 19, Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 91.96 | 93.97 | 106.8 |
| 1 | 20 | in foil | 92.19 | 94.22 | 107.1 |
| 2 | 20 | in foil | 92.38 | 94.42 | 107.3 |
| 4 | 20 | in foil | 92.34 | 94.39 | 107.2 |
| 7 | 20 | in foil | 92.31 | 94.34 | 107 |
| 24 | 20 | in foil | 92.35 | 94.36 | 107.1 |
| 48 | 20 | in foil | 92.37 | 94.41 | 107.1 |
| 120 | 20 | in foil | 92.1 | 94.09 | 106.2 |
| 192 | 20 | in foil | 92.67 | 94.74 | 107.2 |
| 0 | 20 | Exposed | 92.42 | 94.45 | 107.5 |
| 1 | 20 | Exposed | 92.3 | 94.29 | 107 |
| 2 | 20 | Exposed | 91.75 | 93.73 | 106 |
| 4 | 20 | Exposed | 91.47 | 93.34 | 105 |
| 7 | 20 | Exposed | 90.46 | 92.26 | 102.9 |
| 24 | 20 | Exposed | 86.73 | 88.13 | 95.52 |
| 48 | 20 | Exposed | 85 | 86.37 | 92.73 |
| 120 | 20 | Exposed | 81.99 | 83.42 | 86.85 |
| 192 | 20 | Exposed | 78.21 | 79.67 | 80.46 |
| 0 | 50 | Exposed | 92.16 | 94.17 | 107.2 |
| 1 | 50 | Exposed | 92.04 | 94.03 | 106.8 |
| 2 | 50 | Exposed | 92.12 | 94.06 | 106.4 |
| 4 | 50 | Exposed | 90.66 | 92.45 | 103.7 |
| 7 | 50 | Exposed | 88.7 | 90.16 | 99.81 |
| 24 | 50 | Exposed | 81.22 | 82.19 | 87.46 |
| 48 | 50 | Exposed | 77.65 | 78.57 | 80.7 |
| 120 | 50 | Exposed | 71.24 | 71.74 | 67.76 |
| 192 | 50 | Exposed | 69.16 | 69.42 | 62.4 |

Example 20

Samples were prepared in same way as Example 16, except the silver sulfate solution was prepared by placing 1.156 g silver sulfate and 200 g distilled water in a glass bottle. This resulting silver sulfate solution was approximately 4000 µg Ag/g. The color of the samples was white in appearance. The results from color monitoring experiments using this coating solution are shown in Table 10. Exposure conditions are as indicated in Example 16.

TABLE 10

Example 20 Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 90.45 | 92.48 | 105.5 |
| 1 | 20 | in foil | 91.21 | 93.24 | 106 |
| 2 | 20 | in foil | 91.1 | 93.16 | 105.9 |
| 4 | 20 | in foil | 91.2 | 93.26 | 106 |
| 7 | 20 | in foil | 91.14 | 93.18 | 106 |
| 24 | 20 | in foil | 91.12 | 93.17 | 106.1 |
| 48 | 20 | in foil | 91.3 | 93.4 | 106.3 |
| 0 | 20 | Exposed | 92.23 | 94.24 | 107.7 |
| 1 | 20 | Exposed | 91.87 | 93.86 | 106.7 |
| 2 | 20 | Exposed | 91.49 | 93.42 | 105.9 |
| 4 | 20 | Exposed | 90.66 | 92.47 | 104.2 |
| 7 | 20 | Exposed | 89.06 | 90.66 | 100.7 |
| 24 | 20 | Exposed | 84.15 | 85.42 | 93.06 |
| 48 | 20 | Exposed | 81.19 | 82.56 | 88.75 |
| 0 | 50 | Exposed | 92.04 | 94.03 | 107.2 |
| 1 | 50 | Exposed | 91.58 | 93.56 | 106.2 |
| 2 | 50 | Exposed | 91.33 | 93.23 | 105.3 |
| 4 | 50 | Exposed | 90.24 | 91.98 | 103 |
| 7 | 50 | Exposed | 88.58 | 90.09 | 99.58 |
| 24 | 50 | Exposed | 83.66 | 84.79 | 90.68 |
| 48 | 50 | Exposed | 81.12 | 82.21 | 85.22 |

Example 21

Samples were prepared in same way as Example 16, except the drying temperature was 170° C. The resulting material was yellow in color. The results from color monitoring experiments are shown in Table 11. Exposure conditions are as indicated in Example 16.

TABLE 11

Example 21 Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 57.16 | 57.26 | 27.52 |
| 2 | 20 | in foil | 57.31 | 57.41 | 27.66 |
| 4 | 20 | in foil | 57.46 | 57.58 | 27.78 |
| 7 | 20 | in foil | 58.09 | 58.28 | 28.43 |
| 24 | 20 | in foil | 58.44 | 58.68 | 28.92 |
| 48 | 20 | in foil | 57.37 | 57.35 | 27.06 |
| 0 | 20 | Exposed | 58.03 | 58.24 | 27.91 |
| 2 | 20 | Exposed | 59.26 | 59.66 | 28.72 |
| 4 | 20 | Exposed | 58.81 | 59.15 | 28.26 |
| 7 | 20 | Exposed | 58.61 | 58.89 | 28.02 |
| 24 | 20 | Exposed | 58.56 | 58.78 | 27.89 |
| 48 | 20 | exposed | 58.33 | 58.53 | 27.62 |
| 0 | 50 | exposed | 58.25 | 58.56 | 29.17 |
| 2 | 50 | exposed | 58.91 | 59.28 | 29.38 |
| 4 | 50 | exposed | 58.76 | 59.15 | 28.92 |
| 7 | 50 | exposed | 59.11 | 59.48 | 29.39 |
| 24 | 50 | exposed | 57.62 | 57.77 | 27.9 |
| 48 | 50 | exposed | 56.95 | 57.01 | 27.03 |

Example 22

Samples were prepared in same way as Example 17, except the drying temperature was 170° C. The resulting material was golden yellow in color. The results from color monitoring experiments are shown in Table 12. Exposure conditions are as indicated in Example 16.

TABLE 12

Example 22 Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 49.97 | 48.85 | 20.94 |
| 2 | 20 | in foil | 49.74 | 48.56 | 20.65 |
| 4 | 20 | in foil | 50.57 | 49.47 | 21.27 |
| 7 | 20 | in foil | 50.06 | 48.89 | 20.95 |
| 24 | 20 | in foil | 50.57 | 49.45 | 21.21 |
| 48 | 20 | in foil | 50.2 | 49.02 | 21.01 |
| 120 | 20 | in foil | 51.07 | 49.95 | 21.42 |
| 0 | 20 | Exposed | 49.97 | 48.9 | 21.73 |
| 2 | 20 | Exposed | 49.24 | 48.1 | 20.94 |
| 4 | 20 | Exposed | 49.92 | 48.81 | 21.75 |
| 7 | 20 | Exposed | 48.96 | 47.85 | 20.91 |
| 24 | 20 | Exposed | 49.09 | 47.86 | 20.89 |
| 48 | 20 | Exposed | 48.67 | 47.44 | 20.67 |
| 120 | 20 | Exposed | 48.54 | 47.22 | 20.88 |
| 0 | 50 | Exposed | 51.32 | 50.58 | 22.21 |
| 2 | 50 | Exposed | 53.11 | 52.61 | 22.86 |
| 4 | 50 | Exposed | 52.72 | 52.15 | 22.68 |
| 7 | 50 | Exposed | 51.53 | 50.76 | 21.42 |
| 24 | 50 | Exposed | 51.14 | 50.26 | 21.38 |
| 48 | 50 | Exposed | 49.69 | 48.63 | 20.28 |
| 120 | 50 | Exposed | 47.75 | 46.56 | 19.06 |

The resulting samples from Example 22 that were stored at 20% relative humidity were measured for silver release into a solution of distilled water and sodium nitrate using a silver ion selective electrode (Orion, available VWR International, Batavia, Ill.). A sample (0.0962 g) from Example 22 that was exposed to light for 120 hr at approximately 20% relative humidity released 4.9 mg silver ion per gram of sample within 30 minutes of placing the sample in 98 grams distilled water and 2.96 grams of 5M sodium nitrate. A sample (0.0954 g) from Example 22 that was not exposed to light (in foil for 120 hrs) released 4.6 mg silver ion per gram of sample within 30 minutes of placing the sample in 98 grams distilled water and 2.96 grams of 5M sodium nitrate.

Example 23

Samples were prepared in same way as Example 19, except the drying temperature was 170° C. The resulting material was golden yellow in color. The results from color monitoring experiments are shown in Table 13. Exposure conditions are as indicated in Example 16.

TABLE 13

Example 23 Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 42.12 | 40.09 | 17.59 |
| 2 | 20 | in foil | 41.93 | 40.02 | 16.83 |
| 4 | 20 | in foil | 41.17 | 39.18 | 16.35 |
| 7 | 20 | in foil | 42.1 | 40.23 | 16.9 |
| 24 | 20 | in foil | 43.15 | 41.38 | 17.76 |
| 48 | 20 | in foil | 41.48 | 39.48 | 16.55 |
| 120 | 20 | in foil | 42.06 | 40.12 | 16.98 |
| 192 | 20 | in foil | 42.52 | 40.55 | 17.23 |
| 0 | 20 | exposed | 38.21 | 36.11 | 15.52 |
| 2 | 20 | exposed | 38.31 | 36.24 | 15.97 |
| 4 | 20 | exposed | 38.42 | 36.33 | 15.58 |
| 7 | 20 | exposed | 37.91 | 35.8 | 15.37 |
| 24 | 20 | exposed | 37.79 | 35.63 | 15.15 |

TABLE 13-continued

Example 23 Color with Time

| Exposure Time (hr) | Relative Humidity (% RH) | Exposure conditions | CIE Tristimulus Values | | |
|---|---|---|---|---|---|
| | | | X | Y | Z |
| 48 | 20 | exposed | 36.8 | 34.58 | 14.81 |
| 120 | 20 | exposed | 36.3 | 34.04 | 14.24 |
| 192 | 20 | exposed | 35.92 | 33.65 | 13.91 |
| 0 | 50 | exposed | 39.65 | 37.53 | 15.72 |
| 2 | 50 | exposed | 42.18 | 40.4 | 16.41 |
| 4 | 50 | exposed | 42.06 | 40.2 | 16.13 |
| 7 | 50 | exposed | 41.22 | 39.31 | 15.8 |
| 24 | 50 | exposed | 38.2 | 36.02 | 14.43 |
| 48 | 50 | exposed | 37.92 | 35.68 | 14.26 |
| 120 | 50 | exposed | 36.34 | 34.1 | 13.56 |
| 192 | 50 | exposed | 36.03 | 33.82 | 13.07 |

Example 24

Samples were prepared in same way as Example 20, except the drying temperature was 170° C. The resulting material was golden yellow in color. The results from color monitoring experiments are shown in Table 14. Exposure conditions are as indicated in Example 16.

TABLE 14

Example 24 Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 38.32 | 36.03 | 15.68 |
| 2 | 20 | in foil | 38.77 | 36.47 | 15.73 |
| 4 | 20 | in foil | 39.13 | 36.85 | 15.85 |
| 7 | 20 | in foil | 39.12 | 36.8 | 15.83 |
| 24 | 20 | in foil | 38.95 | 36.64 | 15.66 |
| 48 | 20 | in foil | 38.38 | 36.16 | 15.59 |
| 120 | 20 | in foil | 38.86 | 36.54 | 15.85 |
| 192 | 20 | in foil | 39.82 | 37.58 | 16.32 |
| 0 | 20 | exposed | 37.51 | 35.29 | 16.09 |
| 2 | 20 | exposed | 37.31 | 35.13 | 16.05 |
| 4 | 20 | exposed | 36.92 | 34.71 | 16.01 |
| 7 | 20 | exposed | 38.05 | 35.82 | 16.63 |
| 24 | 20 | exposed | 36.18 | 33.91 | 15.86 |
| 48 | 20 | exposed | 35.61 | 33.32 | 15.6 |
| 120 | 20 | exposed | 34.61 | 32.49 | 14.59 |
| 192 | 20 | exposed | 34.8 | 32.5 | 15.12 |
| 0 | 50 | exposed | 36.17 | 34.05 | 15.18 |
| 2 | 50 | exposed | 37.88 | 35.88 | 15.32 |
| 4 | 50 | exposed | 37.63 | 35.6 | 15.1 |
| 7 | 50 | exposed | 37.29 | 35.2 | 14.97 |
| 24 | 50 | exposed | 35.79 | 33.59 | 14.27 |
| 48 | 50 | exposed | 34.66 | 32.4 | 13.76 |
| 120 | 50 | exposed | 32.82 | 30.49 | 13.07 |
| 192 | 50 | exposed | 32.89 | 30.5 | 13.01 |

Example 25

Samples were prepared in same way as Example 17, except that the substrate was TENCEL/PET, a 70/30 Tencel/Polyester 24 mesh apertured spunlaced non-woven (Grade SX-524, 38 gsm, white) from Green Bay Nonwovens in Green Bay, Wis. that contained less than 40 ppm chloride and the drying temperature was 170° C. The color of the material was a golden yellow color. The results from color monitoring experiments are shown in Table 15. Exposure conditions are as indicated in Example 16.

TABLE 15

Example 25 Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 37.23 | 35.79 | 16.25 |
| 2 | 20 | in foil | 38.07 | 36.47 | 15.81 |
| 4 | 20 | in foil | 39.84 | 38.41 | 16.76 |
| 7 | 20 | in foil | 38.71 | 37.19 | 15.88 |
| 24 | 20 | in foil | 39.11 | 37.55 | 15.98 |
| 48 | 20 | in foil | 38.42 | 36.8 | 14.91 |
| 120 | 20 | in foil | 36.91 | 35.16 | 14.51 |
| 0 | 20 | exposed | 36.51 | 34.87 | 15.2 |
| 2 | 20 | exposed | 36.29 | 34.87 | 15.96 |
| 4 | 20 | exposed | 36.68 | 35.34 | 16.89 |
| 7 | 20 | exposed | 35.28 | 33.9 | 15.2 |
| 24 | 20 | exposed | 32.79 | 31.6 | 14.43 |
| 48 | 20 | exposed | 33.43 | 32.43 | 16.01 |
| 120 | 20 | exposed | 32.65 | 31.67 | 15.56 |
| 0 | 50 | exposed | 35.24 | 33.46 | 14.66 |
| 2 | 50 | exposed | 36.9 | 35.8 | 17.16 |
| 4 | 50 | exposed | 33.12 | 32.08 | 15.61 |
| 7 | 50 | exposed | 31.04 | 30.15 | 14.46 |
| 24 | 50 | exposed | 28.37 | 27.87 | 14.63 |
| 48 | 50 | exposed | 25.17 | 24.84 | 13.19 |
| 120 | 50 | exposed | 27.58 | 27.55 | 16.21 |

The resulting samples from Example 25 that were stored at 20% relative humidity were measured for silver release into a solution of distilled water and sodium nitrate using a silver ion selective electrode (Orion, available VWR International, Batavia, Ill.). A sample (0.0992 g) from Example 25 that was exposed to light for 120 hr at approximately 20% relative humidity released 4.9 mg silver ion per gram of sample within 30 minutes of placing the sample in 98 grams distilled water and 2.96 grams of 5M sodium nitrate. A sample (0.0949 g) from Example 25 that was not exposed to light (in foil for 120 hrs) released 4.7 mg silver ion per gram of sample within 30 minutes of placing the sample in 98 grams distilled water and 2.96 grams of 5M sodium nitrate.

Example 26

Samples were prepared in same way as Example 17, except substrate was a 4.375-inch by a 4.375-inch (11.11 cm×11.11 cm) piece of 100% cotton non-woven from Suntec Union, Japan (Nissinbo, AN20601050, 60 gsm), the drying temperature was 170° C. and controlled samples were placed in a foil pouch. The color of the material was a golden yellow color. The results from color monitoring experiments are shown in Table 16. Exposure conditions are as indicated in Example 16.

TABLE 16

Example 26 Color with Time

| Exposure Time (days) | Relative Humidity (% RH) | Exposure conditions | CIE Tristimulus Values | | |
|---|---|---|---|---|---|
| | | | X | Y | Z |
| initial | 20 | in foil pouch | 42.6 | 41.3 | 16.48 |
| 9 | 20 | in foil pouch | 43.46 | 42.14 | 16.67 |
| 14 | 20 | in foil pouch | 41.84 | 39.97 | 15.36 |
| 17 | 20 | in foil pouch | 41.2 | 39.3 | 15.58 |
| 20 | 20 | in foil pouch | 41.79 | 39.88 | 15.61 |
| 24 | 20 | in foil pouch | 42.42 | 40.59 | 15.82 |
| 1 | 20 | exposed | 42.23 | 41.01 | 16.65 |
| 9 | 20 | exposed | 41.06 | 39.64 | 15.85 |

TABLE 16-continued

Example 26 Color with Time

| Exposure Time (days) | Relative Humidity (% RH) | Exposure conditions | CIE Tristimulus Values | | |
|---|---|---|---|---|---|
| | | | X | Y | Z |
| 14 | 20 | exposed | 40.36 | 38.87 | 15.33 |
| 17 | 20 | exposed | 40.08 | 38.7 | 15.26 |
| 20 | 20 | exposed | 40.3 | 38.93 | 15.6 |
| 24 | 20 | exposed | 39.55 | 38.21 | 15.18 |
| 1 | 50 | exposed | 42.06 | 40.79 | 15.62 |
| 9 | 50 | exposed | 38.66 | 37.32 | 14.38 |
| 14 | 50 | exposed | 37.85 | 36.59 | 13.92 |
| 17 | 50 | exposed | 37.07 | 36.09 | 14.55 |
| 20 | 50 | exposed | 36.62 | 35.63 | 13.86 |
| 24 | 50 | exposed | 36.85 | 35.97 | 14.14 |

Example 27

Samples were prepared in same way as Example 23, except the substrate was TENCEL, a non-woven of 100% Tencel fibers (SX-152, white, 65 gsm, 24 mesh) from Green Bay Nonwovens, Inc. in Green Bay, Wis. that contained less than 40 ppm chloride. The resulting material was golden yellow in color. The results from color monitoring experiments are shown in Table 17. Exposure conditions are as indicated in Example 16.

TABLE 17

Example 27 Color with Time

| Exposure Time (hr) | Relative Humidity (% RH) | Exposure conditions | CIE Tristimulus Values | | |
|---|---|---|---|---|---|
| | | | X | Y | Z |
| 0 | 20 | in foil | 26.72 | 24.69 | 7.44 |
| 2 | 20 | in foil | 26.93 | 24.92 | 7.56 |
| 4 | 20 | in foil | 26.98 | 24.95 | 7.44 |
| 7 | 20 | in foil | 27.23 | 25.22 | 7.53 |
| 22 | 20 | in foil | 27.79 | 25.8 | 7.92 |
| 0 | 20 | exposed | 25.82 | 23.87 | 7.54 |
| 2 | 20 | exposed | 28.46 | 26.53 | 9.41 |
| 4 | 20 | exposed | 28.85 | 26.92 | 9.51 |
| 7 | 20 | exposed | 28.37 | 26.45 | 9.48 |
| 22 | 20 | exposed | 27.14 | 25.39 | 8.46 |
| 0 | 20 | exposed | 25.2 | 23.21 | 6.67 |
| 2 | 20 | exposed | 25.99 | 23.91 | 6.81 |
| 4 | 20 | exposed | 25.01 | 23.09 | 6.59 |
| 7 | 20 | exposed | 23.95 | 22.2 | 6.49 |
| 22 | 20 | exposed | 22.47 | 21.07 | 6.86 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of making an antimicrobial wound dressing, the method comprising:
    preparing a composition comprising silver sulfate and water; wherein any stabilizing agent is present in an amount less than 50 ppm based on the total weight of the silver sulfate composition;
    coating the silver sulfate composition on a cellulosic substrate;
    drying the coated substrate at a temperature of 125° C. to 190° C., such that the coated substrate darkens in proportion to the temperature, turning to a yellow color, a brown color, or a dark brown color;
    wherein after drying, the composition includes less than 20 wt % silver metal, based on the total weight of silver components in the composition; and
    maintaining the dried silver sulfate coated substrate at a relative humidity of no more than 50%;
    wherein the dry antimicrobial wound dressing is color stable.

2. The method of claim 1, wherein the cellulosic substrate comprises cotton.

3. The method of claim 1, wherein the silver sulfate composition further comprises silver compounds other than silver sulfate.

4. The method of claim 3, wherein the silver compounds are selected from the group consisting of silver oxide, silver nitrate, silver acetate, silver citrate, silver chloride, silver lactate, silver phosphate, silver stearate, silver thiocyanate, silver carbonate, silver saccharinate, silver anthranilate and combinations thereof.

5. The method of claim 3, wherein the silver sulfate is present in an amount of at least 60 wt % of the composition based on the total weight of the silver components of the composition.

6. The method of claim 1, wherein the pH of the silver sulfate coating composition is at least 4.

7. The method of claim 6, wherein the pH of the coating composition is no greater than 9.

8. The method of claim 1, wherein the silver sulfate composition is free of any acid.

9. The method of claim 1, wherein the substrate is a nonwoven gauze, a woven gauze, a film, or a hydrocolloid.

10. The method of claim 1, wherein the silver sulfate composition further comprises methanol, ethanol, isopropanol, acetone, or an organic solvent that is miscible with water.

11. A method of making an antimicrobial wound dressing, the method comprising:
    preparing a composition comprising silver sulfate and water; wherein any stabilizing agent is present in an amount less than 50 ppm based on the total weight of the silver sulfate composition
    coating the silver sulfate composition on a cellulosic substrate;
    drying the coated substrate at a temperature of 125° C. to 190° C. such that the coated substrate changes color to a color is selected from the group consisting of yellow, gold, tan, and brown; wherein the dried composition includes less than 20 wt % silver metal, based on the total weight of silver components in the composition;
    wherein the dry antimicrobial wound dressing is color stable.

12. The method of claim 11, wherein the antimicrobial wound dressing is maintained in an environment of no more than 50% relative humidity at room temperature.

13. The method of claim 12, wherein the antimicrobial wound dressing is maintained in an environment of no more than 20% relative humidity at room temperature.

14. The method of claim 11, wherein the silver sulfate composition further comprises silver compounds other than silver sulfate.

15. The method of claim 14, wherein the silver compounds are selected from the group consisting of silver oxide, silver nitrate, silver acetate, silver citrate, silver chloride, silver lactate, silver phosphate, silver stearate, silver thiocyanate, silver carbonate, silver saccharinate, silver anthranilate and combinations thereof.

16. The method of claim 14, wherein the silver compounds comprise less than 20 wt % of the composition, based on the total weight of the silver components of the composition.

17. The method of claim 11, wherein the silver sulfate is present in an amount of at least 60 wt % of the composition, based on the total weight of the silver components of the composition.

18. The method of claim 17, wherein the silver sulfate is present in an amount of at least 90 wt % of the composition, based on the total weight of the silver components of the composition.

19. The method of claim 11, wherein the pH of the coating composition is at least 4.

20. The method of claim 11, wherein the pH of the coating composition is no greater than 9.

21. The method of claim 11, wherein the silver sulfate composition is free of any acid.

22. The method of claim 11, wherein the drying is carried out at a temperature of less than 170° C.

23. The method of claim 11, wherein the drying is carried out at a temperature of at least 140° C.

24. The method of claim 11, wherein the substrate is a nonwoven gauze, a woven gauze, a film, or a hydrocolloid.

25. The method of claim 24, wherein the cellulosic substrate comprises cotton.

26. The method of claim 1, wherein the drying is carried out at a temperature of less than 190° C.

27. The method of claim 26, wherein the drying is carried out at a temperature of less than 170° C.

28. The method of claim 1, wherein the drying is carried out at a temperature of 140° C. to 170° C.

* * * * *